(12) United States Patent
Takii et al.

(10) Patent No.: US 7,267,800 B2
(45) Date of Patent: Sep. 11, 2007

(54) DRAINAGE SYSTEM

(75) Inventors: Tadaoki Takii, Kanagawa-ken (JP);
Atsushi Inami, Kanagawa-ken (JP)

(73) Assignee: Shimadzu Corporation, Kyoto-shi (JP)

( * ) Notice: Subject to any disclaimer, the term of this patent is extended or adjusted under 35 U.S.C. 154(b) by 207 days.

(21) Appl. No.: 09/875,184

(22) Filed: Jun. 7, 2001

(65) Prior Publication Data

US 2001/0055545 A1 Dec. 27, 2001

(30) Foreign Application Priority Data

Jun. 22, 2000 (JP) ............................ 2000-187928

(51) Int. Cl.
*B01L 3/02* (2006.01)
*G01N 1/10* (2006.01)

(52) U.S. Cl. ................. 422/100; 422/101; 73/863.32; 73/863.54; 73/863.83; 73/864; 73/864.11; 73/864.24; 73/864.25

(58) Field of Classification Search ............... 422/99, 422/103, 100, 101; 210/222; 209/213; 73/863.32, 73/863.33, 863.71, 863.72, 864, 864.01, 73/864.02, 864.11, 864.15, 864.17, 864.24, 73/864.25, 864.31, 863.54, 863.83, 864.34
See application file for complete search history.

(56) References Cited

U.S. PATENT DOCUMENTS

| | | | | |
|---|---|---|---|---|
| 4,879,242 A | | 11/1989 | Tsukioka | ..................... 436/54 |
| 5,240,679 A | * | 8/1993 | Stettler | ........................ 422/67 |
| 5,273,717 A | * | 12/1993 | Marvin | ....................... 422/100 |
| 5,275,951 A | * | 1/1994 | Chow et al. | .................. 436/50 |
| 5,334,353 A | * | 8/1994 | Blattner | ..................... 422/100 |
| 5,443,791 A | * | 8/1995 | Cathcart et al. | .............. 422/65 |
| 5,558,839 A | * | 9/1996 | Matte et al. | ................. 422/101 |
| 5,578,495 A | * | 11/1996 | Wilks | ......................... 436/178 |
| 5,660,792 A | * | 8/1997 | Koike | .......................... 422/63 |
| 5,779,907 A | * | 7/1998 | Yu | ............................. 210/695 |
| 5,853,665 A | * | 12/1998 | Ade et al. | ..................... 422/62 |
| 5,895,631 A | * | 4/1999 | Tajima | ....................... 422/101 |
| 5,904,899 A | * | 5/1999 | Hayashi | ....................... 422/65 |
| 6,033,911 A | * | 3/2000 | Schultz et al. | ................ 436/49 |
| 6,190,614 B1 | * | 2/2001 | Fukunaga | .................... 422/100 |
| 6,194,160 B1 | * | 2/2001 | Levin | .......................... 435/7.1 |
| 6,240,984 B1 | * | 6/2001 | Fawcett et al. | .............. 141/130 |
| 6,241,947 B1 | * | 6/2001 | Komatsu et al. | .............. 422/67 |
| 6,269,846 B1 | * | 8/2001 | Overbeck et al. | .............. 141/1 |

(Continued)

FOREIGN PATENT DOCUMENTS

CN 2139854 Y 8/1993

OTHER PUBLICATIONS

WO 00/08474 Bienert et al.; Feb. 17, 2000.*

*Primary Examiner*—Brian R. Gordon
(74) *Attorney, Agent, or Firm*—Westerman, Hattori, Daniels & Adrian, LLP.

(57) ABSTRACT

In a system for sucking and discharging a solution from a vessel (micro-plate assembly 6) by suction nozzles 2, processes for suction, discharge, separation, etc. can be carried out with use of a simple mechanism, including suction nozzle moving means 3 for positioning the respective distal ends of the suction nozzles on the inner wall surface of the vessel, magnetic particle holding means 4 for magnetic particles 7 in a given position in the vessel, and solution discharge means 5 for sucking out and discharging the solution simultaneously from the vessel through the suction nozzles. Each or a combination of these means constitutes a drainage system.

3 Claims, 6 Drawing Sheets

U.S. PATENT DOCUMENTS

| | | |
|---|---|---|
| 6,270,726 B1 * | 8/2001 | Tyberg et al. ................ 422/100 |
| 6,309,891 B1 * | 10/2001 | Shalon et al. ............... 436/180 |
| 6,368,561 B1 * | 4/2002 | Rutishauser et al. .......... 422/99 |
| 6,447,728 B1 * | 9/2002 | Wilmes et al. .............. 422/100 |
| 6,455,325 B1 * | 9/2002 | Tajima ....................... 436/526 |
| 6,506,611 B2 * | 1/2003 | Bienert et al. .............. 436/180 |
| 6,569,385 B1 * | 5/2003 | Little et al. ................. 422/100 |
| 6,627,157 B1 * | 9/2003 | Doktycz et al. ............ 422/100 |
| 6,645,431 B2 * | 11/2003 | Astle ............................ 422/99 |
| 6,672,458 B2 * | 1/2004 | Hansen et al. .............. 209/224 |
| 6,824,024 B2 * | 11/2004 | Ingenhoven et al. ........ 222/504 |
| 2002/0098121 A1 * | 7/2002 | Astle ............................ 422/99 |
| 2002/0173048 A1 * | 11/2002 | Nakazawa et al. .......... 436/180 |
| 2002/0192113 A1 * | 12/2002 | Uffenheimer et al. ......... 422/67 |
| 2004/0067165 A1 * | 4/2004 | Isobe et al. ................... 422/64 |

\* cited by examiner

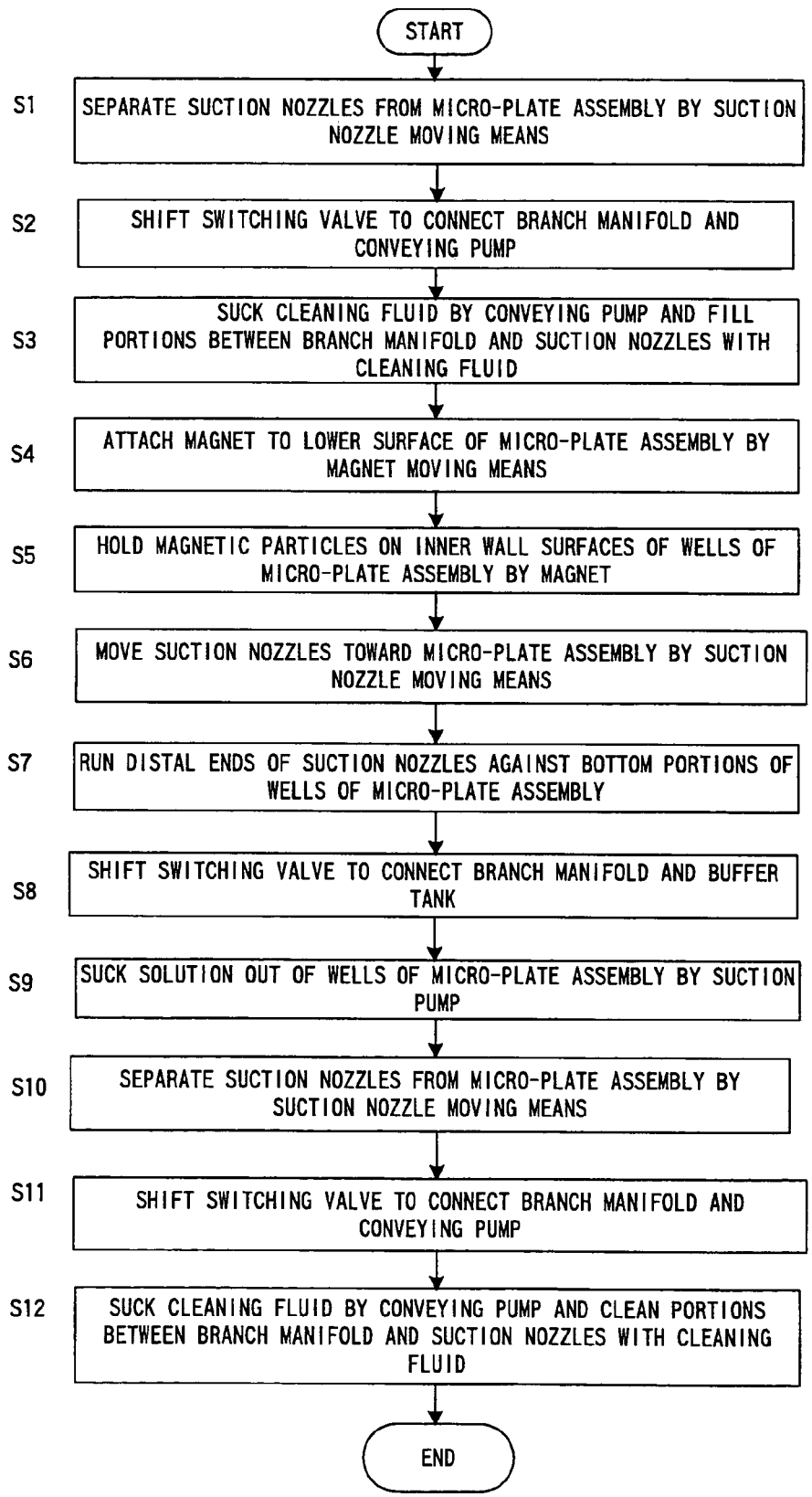

DRAINAGE SYSTEM

BACKGROUND OF THE INVENTION

1. Field of the Invention

The present invention relates to a drainage system for carrying out treatments that are required in predetermined processes for reagent addition, liquid suction, discharge, and separation, etc., using a vessel.

2. Description of the Prior Art

In the fields of clinical chemistry, biochemistry, pharmaceutical chemistry, etc. that involve chemical analyses, various treatments, such as reagent addition, liquid suction, discharge, and separation, etc., are carried out in reaction processes. In the case where a liquid sample in a vessel, such as a micro-plate assembly or vial, contains an objective substance, for example, magnetic particles that serve to hold the objective substance on their respective surfaces are loaded into the liquid sample. After the objective substance is held on the magnetic particles, supernatant liquid is sucked out and discharged, whereby the objective substance can be separated from the liquid sample.

In this treatment, only the supernatant liquid is sucked out and discharged while the magnetic particles that hold the objective substance are not discharged. For this purpose, a magnet is brought close to the vessel to collect the magnet particles in one place.

A conventional treatment such as separation treatment using magnet particles is carried out by manual operation or by using suction mechanism provided with a plurality of plungers.

A conventional treatment such as manual separation requires troublesome operations, such as operation for bringing the magnet close to the vessel and operation for discharging supernatant liquid by a pipette or the like. In the case where a large number of minute vessels, such as micro-plates, vials, etc., are arranged for the treatment, the treatment takes a long time.

On the other hand, a system in which a suction mechanism with a plurality of plungers are used for automatic separation requires an actuator that entails high-accuracy control for each plunger, in order to actuate a plurality of micropipettes by the plungers. Thus, the system is complicated and expensive.

OBJECT AND SUMMARY OF THE INVENTION

The object of the present invention is to provide a drainage system capable of carrying out processes for suction, discharge, separation, etc. with use of a simple mechanism.

In order to achieve the above object, a drainage system in a first aspect of the present invention comprises a suction nozzle for sucking and discharging a solution from a vessel and suction nozzle moving means. The suction nozzle moving means includes support means for supporting the suction nozzle for movement toward the vessel and urging means for urging the suction nozzle toward the vessel. The suction nozzle moving means can position the suction nozzle with its distal end in contact with the inner wall surface of the vessel.

In this first aspect of the invention, the support means brings the suction nozzle close to the vessel so that the distal end of the nozzle touches the inner wall surface of the bottom portion of the vessel. The suction nozzle is urged toward the vessel by the urging means, and the support means supports the suction nozzle for movement. If the support means is further moved toward the vessel after the suction nozzle touches the inner wall surface of the bottom portion of the vessel, therefore, the nozzle end can be kept in contact with the inner wall surface of the bottom portion. In this state, the suction nozzle sucks and discharges the solution from the vessel. In separating the suction nozzle from the vessel after the solution is sucked and discharged, the nozzle, which is urged toward the vessel by the urging means, is allowed naturally to return to its initial position.

Thus, with use of the suction nozzle moving means, the suction nozzle can be positioned on the bottom portion of the vessel without requiring positioning control for the suction nozzle. Further, the residual quantity of the solution can be reduced by positioning the suction nozzle on the bottom portion of the vessel.

A drainage system in a second aspect of the invention comprises a suction nozzle for sucking and discharging a solution from a vessel and magnetic particle holding means. The magnetic particle holding means includes a magnet and magnet moving means for supporting the magnet so as to be movable toward and away from the vessel. The magnet moving means of the magnetic particle holding means can bring the magnet toward the vessel, and the magnet can hold magnetic particles in a given position in the vessel.

If the magnet is brought close to the vessel by the magnet moving means, in this second aspect of the invention, the magnetic particles that hold an objective substance in the vessel are automatically collected on the inner wall surface of the vessel. The position in which the magnetic particles are collected is settled depending on the position where the magnet is brought close to the vessel. Only the solution in the vessel can be sucked out by shifting the distal end position of the suction nozzle from the position where the magnetic particles are collected.

An example of the magnet moving means may be provided with an eccentric cam such that the magnet can be moved toward and away from the vessel by displacing the magnet toward the vessel by the cam.

A drainage system in a third aspect of the invention comprises a plurality of suction nozzles for sucking and discharging a solution from a vessel and solution discharge means. The solution discharge means includes a branch manifold connecting the suction nozzles individually to branch ends by pipes, a suction pump for suction from the suction nozzles through the branch manifold, and liquid conveying means for feeding a liquid into the pipes between the branch manifold and each of the suction nozzles, thereby filling the pipes with the liquid. The solution discharge means simultaneously sucks and discharges the solution from the vessel through the suction nozzles and the branch manifold as the suction pump is operated for suction.

In this third aspect of the invention, suction of solution by one suction pump through a plurality of suction nozzles is realized by connecting those suction nozzles to a branch manifold. Further, by filing the pipes between the branch manifold and each of the suction nozzles with the liquid by the liquid conveying means, the solution in the vessel can be sucked and discharged simultaneously from the suction nozzles without causing empty suction where only air is sucked out, even if any part of the vessel is empty, According to an example of the solution discharge means, an appropriate capacity and resistance are secured between the suction pump and the branch manifold, and further an appropriate capacity is secured between the branch manifold and the suction pipe. If the capacity of spaces between the suction nozzles and each of the branch manifold is made greater than the capacity of the vessel, a negative pressure can be secured in the branch manifold before all the solution in the vessel is sucked out, so that stable suction can be maintained. Further, a proper suction speed can be obtained by securing a suitable resistance between the suction nozzles and the branch manifold.

Furthermore, the capacity of the spaces between the branch manifold and the suction pump can absorb a sudden pressure change that is caused when the operation of the suction pump is started or stopped, thereby slowing down the start and stop of the suction by the suction nozzles, thereby preventing the magnetic particles from being discharged from the vessel. The proper suction speed can be also obtained by securing a suitable resistance between the branch manifold and the suction pump.

In order to secure an appropriate capacity and resistance between the branch manifold and the suction pump, pipes or a buffer tank with a proper capacity may be connected between the branch manifold and the suction pump.

A drainage system in a fourth aspect of the invention comprises all of the aforesaid means including the suction nozzle moving means, magnetic particle holding means, and solution discharge means.

BRIEF DESCRIPTION OF THE DRAWINGS

The foregoing and other objects and features of the invention will become apparent from the following description of preferred embodiments of the invention with reference to the accompanying drawings, in which:

FIG. 2 is a flowchart for illustrating the operation of the drainage system of FIG. 1;

DETAILED DESCRIPTION OF THE PREFERRED EMBODIMENTS

Figure 1:
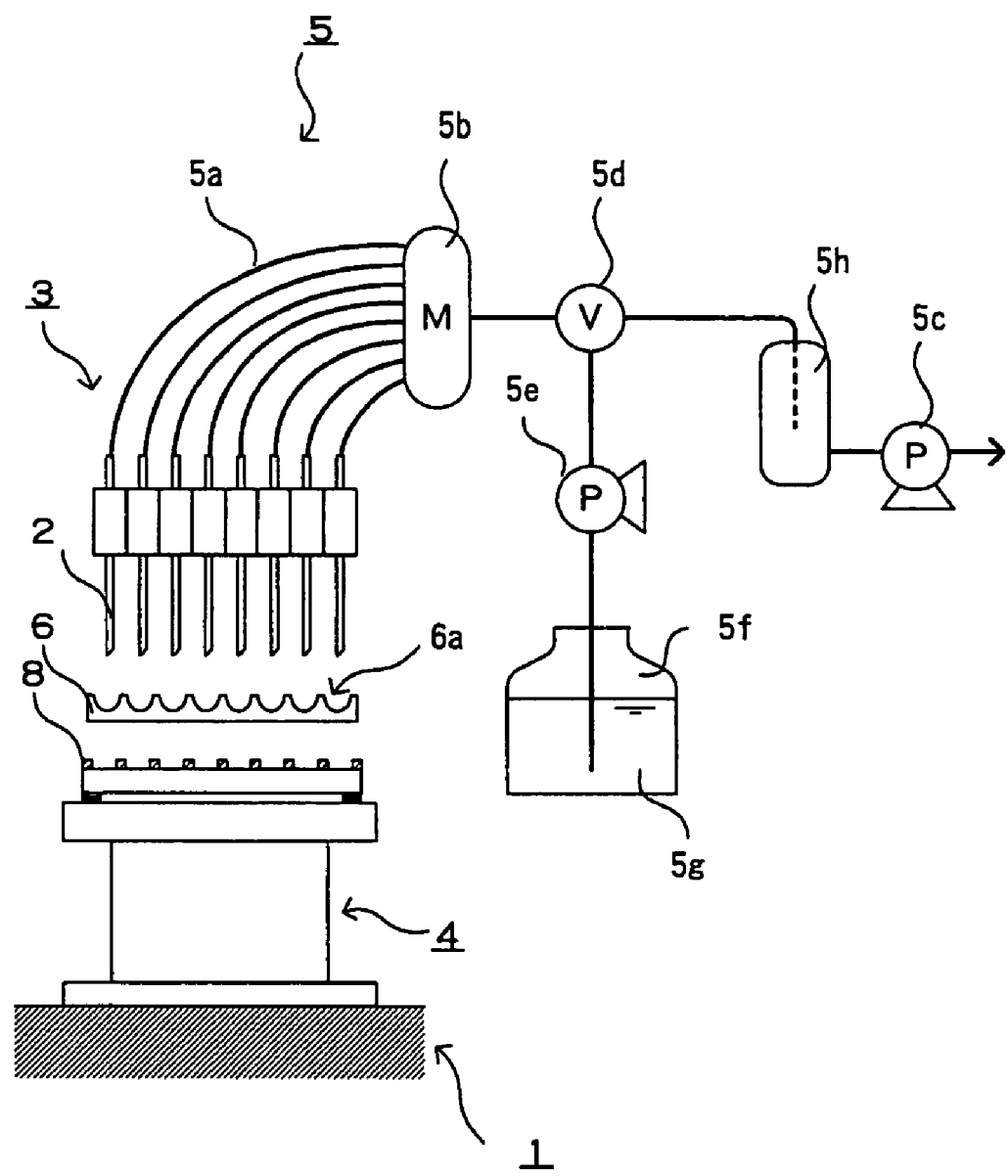
FIG. 1 is a view for illustrating an outline of the construction of a drainage system according to the present invention.

An outline of a drainage system according to the present invention will be described with reference to FIG. 1.

A drainage system 1 comprises a plurality of suction nozzles 2, suction nozzle moving means 3, magnetic particle holding means 4, and solution discharge means 5. The moving means 3 moves the suction nozzles 2 toward or away from a vessel 6 such as a micro-plate assembly. The holding means 4 holds magnetic particles in the vessel 6, thereby preventing the magnetic particles from being sucked out through the nozzles 2. The discharge means 5 causes the suction nozzles 2 to suck solution out of the vessel 6 and discharge solution into the vessel 6.

The vessel 6 is not limited to the micro-plate assembly, and may alternatively be any other vessel such as a vial that can hold a liquid sample. Magnetic particles for holding an objective substance is put in the vessel 6. In an embodiment of the present invention described below, the micro-plate assembly is used as the vessel 6.

The respective distal ends of the suction nozzles 2 are inserted individually into wells 6a of the micro-plate assembly 6, whereby a solution such as a liquid sample is sucked or discharged. The suction nozzle moving means 3 can easily move the suction nozzles 2 toward or away from the micro-plate assembly 6 and position the nozzles 2 in the wells 6a.

The suction nozzle moving means 3 includes support means for supporting the suction nozzles 2 for movement toward and away from the micro-plate assembly 6 and urging means, such as a spring, for urging the suction nozzles 2 toward the micro-plate assembly 6. The support means moves the suction nozzles 2 toward the micro-plate assembly 6. Further, the urging means locates the respective distal ends of the suction nozzles 2 individually in given positions in the wells 6a of the micro-plate assembly 6 without controlling the position of the support means after the nozzle ends are brought into contact with the wells 6a.

The magnetic particle holding means 4 collects the magnetic particles in the wells 6a of the micro-plate assembly 6 by means of magnetic force and prevents them from being sucked out together with the solution through the suction nozzles 2. The holding means 4 includes magnets 8 arranged opposed to the underside of the micro-plate assembly 6 and a movement mechanism capable of moving the magnets 8 toward and away from the micro-plate assembly 6.

The solution discharge means 5 simultaneously sucks and discharges the solution in the micro-plate assembly 6 through the suction nozzles 2. The discharge means 5 includes a branch manifold 5b with branch ends, pipes 5a individually connecting the branch ends and the suction nozzles 2, a suction pump 5c for suction from the suction nozzles 2 through the manifold 5b, and liquid conveying means (switching valve 5d, conveying pump 5e, cleaning fluid vessel 5f, cleaning fluid 5g, etc.) for feeding the liquid into the pipes 5a to fill them with the liquid.

Since the branch manifold 5b of the solution discharge means 5 is connected with the suction nozzles 2, the liquid can be sucked out by the single suction pump 5c. Further, the pipes 5a that extend between the manifold 5b and the suction nozzles 2 are filled with the liquid by the liquid conveying means. If any of the wells 6a of the micro-plate assembly 6 is empty, therefore, the solution in the wells 6a can be automatically sucked and discharged at the same time through the suction nozzles 2 without causing empty suction in which only air is sucked out.

If the capacity of the pipes 5a that connect the branch manifold 5b and the suction nozzles 2 at the branch ends is made larger than the capacity of the micro-plate assembly 6, for example, the portion ranging from the branch manifold 5b to the suction pump 5c can be kept under negative pressure, so that the whole of the solution in the micro-plate assembly 6 can be sucked out with stability. Further, the suction speed can be properly adjusted by subjecting the pipes 5a to an appropriate resistance.

A buffer tank 5h, for use as means for adjusting the capacities and resistances of the portion on the suction side from the branch manifold 5b, can be provided between the switching valve 5d and the suction pump 5c. The tank 5h has a given capacity and a given resistance such that a sudden pressure change, if any, caused when the operation of the suction pump 5c is started or stopped, can be eased to soften the operation of suction through the suction nozzles 2. If the pump operation is stopped before all the solution in the micro-plate assembly 6 is sucked out, in particular, the solution continues to be sucked out under negative pressure in the buffer tank 5h even after the stoppage of the pump operation, so that the micro-plate assembly 6 can be evacuated. As this is done, the negative pressure lowers with time, so that the suction can be finished gently. Thus, the magnetic particles can be prevented from being sucked out.

The capacities and resistances can be also adjusted by pipes arranged between the branch manifold 5b and the suction pump 5c, in place of the buffer tank 5h.

An outline of the operation of the drainage system 1 will now be described with reference to the flowchart of FIG. 2.

First, in the processes of Steps S1 to S3, the pipes 5a are filled up with the liquid. By doing this, simultaneous suction through the suction nozzles 2 can be carried out without sucking only air even if any of the wells 6a of the micro-plate assembly 6 is empty.

The suction nozzle moving means 3 causes the suction nozzles 2 to move to a position at a distance from the micro-plate assembly 6 (Step S1). Then, the switching valve 5d is shifted to connect the branch manifold 5b and the conveying pump 5e (Step S2). The conveying pump 5e sucks the cleaning fluid 5g out of the cleaning fluid vessel 5f, whereupon the pipes 5a between the branch manifold 5b and the suction nozzles 2 are filled with the cleaning fluid 5g (Step S3).

Figure 3A:
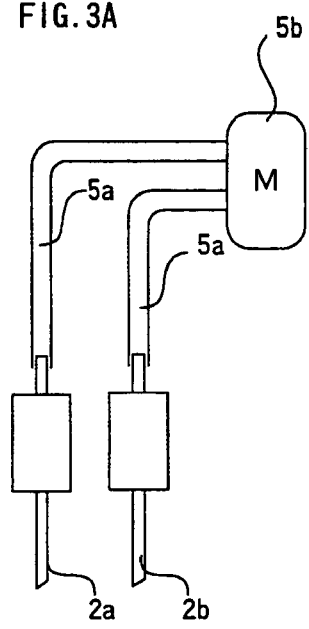
FIGS. 3A to 3D are views for illustrating the operation of suction nozzles of the drainage system of FIG. 1.
Figure 3B:
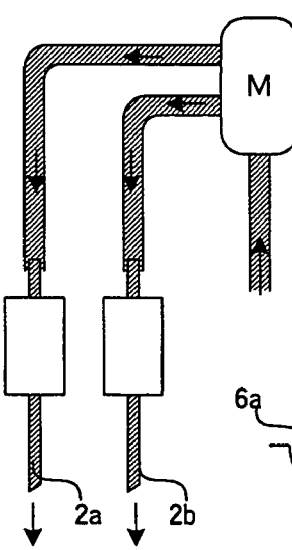
Figure 3C:
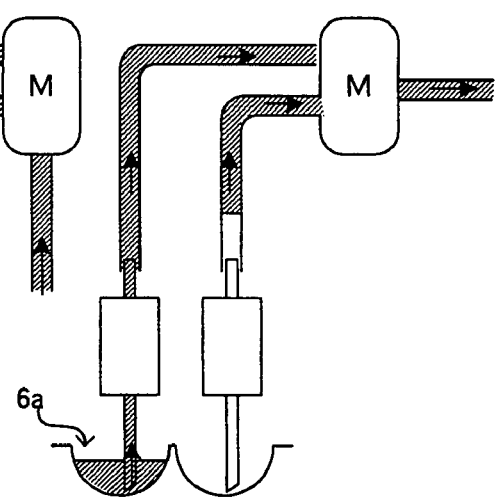

In the process of Step S3, suction nozzles 2a and 2b and the pipes 5a can be shifted from an empty state (FIG. 3A) to a state filled with a liquid (FIG. 3B). Thus, by filling the suction nozzles 2a and 2b and the pipes 5a with the liquid, as shown in FIG. 3B, the liquid in the pipes 5a can be sucked even if one of the wells 6a of the micro-plate assembly 6 is empty, as shown in FIG. 3C. Accordingly, occurrence of a situation where only air is sucked out but liquid in is not sucked out can be avoided. The operation for filling the pipes 5a with the liquid serves also to clean the suction nozzles.

Figure 3D:
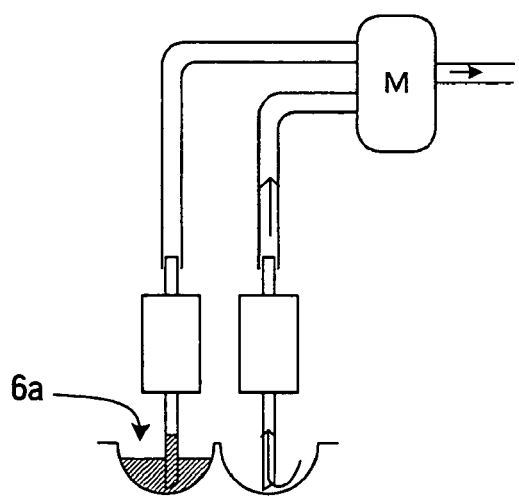

FIG. 3D shows a case in which the solution in the wells 6a is sucked out while the suction nozzles 2a and 2b and the pipes 5a is empty. If one of the wells 6a is empty, in this case, air is sucked out through it. Unless a pump with a high suction speed is used, therefore, the liquid in the other wells 6a cannot be sucked out. Possibly, this suction speed may be too high to prevent the magnetic particles from being sucked in together with the liquid.

Then, the magnetic particle holding means 4 causes the magnets 8 to move toward the underside of the micro-plate assembly 6 (Step S4), whereupon the magnets 8 hold the magnetic particles on the respective inner wall surfaces of the wells 6a of the micro-plate assembly 6 (Step S5).

Figure 4A:
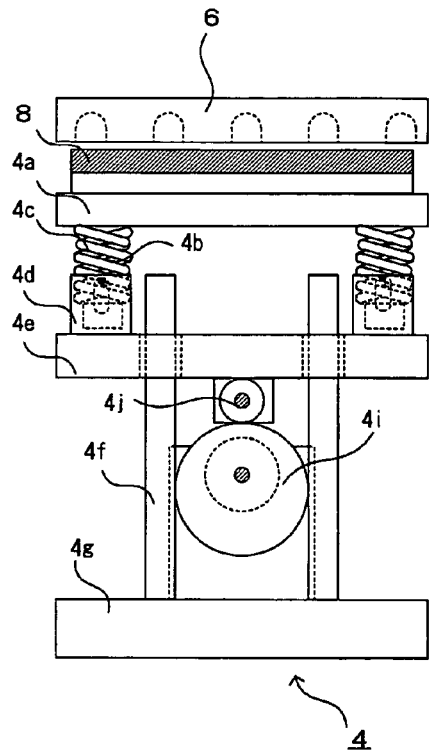
FIGS. 4A and 4B are views for illustrating the configuration and operation of magnetic particle holding means of the drainage system of FIG. 1.
Figure 4B:
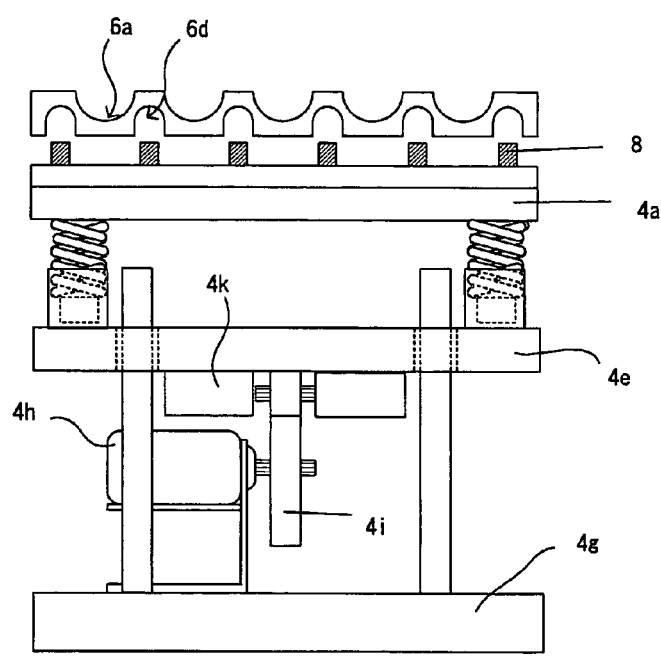
Figure 4C:
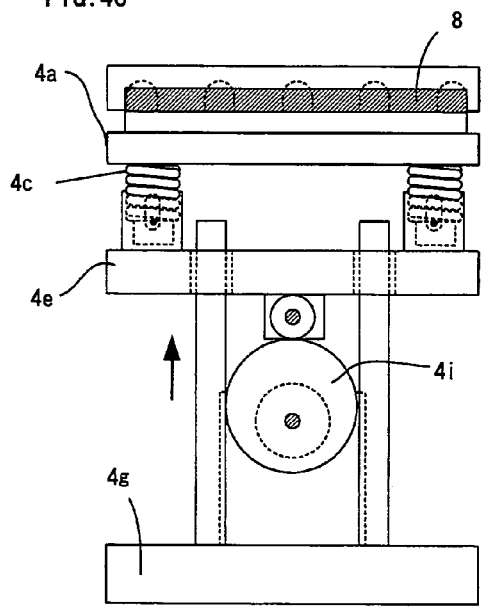
Figure 4D:
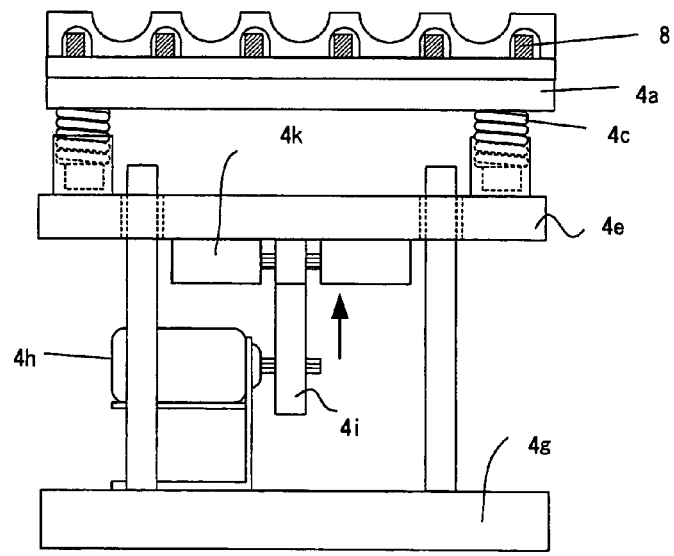

An example of the magnetic particle holding means 4 will now be described with reference to FIGS. 4A to 4C. FIGS. 4A and 4B are a side view and a front view, respectively, of the magnetic particle holding means 4 with the magnets 8 kept away from the micro-plate assembly 6. FIGS. 4C and 4D are a side view and a front view, respectively, of the magnetic particle holding means 4 with the magnets 8 situated close to the micro-plate assembly 6.

The magnetic particle holding means 4 includes a first support plate 4a and a second support plate 4e. The first support plate 4a is fitted with the magnets 8. The support plate 4e moves toward and away from a base 4g (in the vertical direction), guided by a plurality of support posts 4f set up on the base 4g, as an eccentric cam 4i on the base 4g rotates. The second support plate 4e is situated right below the first support plate 4a, and a spring 4c is interposed between these plates 4a and 4e. If the second support plate 4e ascends as the cam 4i rotates, therefore, this motion is transmitted to the first support plate 4a through the spring 4c and causes the plate 4a to ascend. The cam 4i is rotated by a motor 4h that is fixed on the base 4g. The rotation of the eccentric cam 4i causes a bearing 4j and a support member 4k to raise or lower the second support plate 4e.

One end of a shaft 4b is fixed to the first support plate 4a. On the other hand, the second support plate 4e is fitted with a shaft holder 4d, which can receive the distal end portion of the shaft 4b for sliding motion. The spring 4c is mounted on the shaft 4b. Thus, the first support plate 4a is supported over the second support plate 4e by the spring 4c. Alternatively, the shaft 4b and the shaft holder 4d may be attached to the second and first support plates 4e and 4a, respectively.

When the second support plate 4e is moved to its lower position as the eccentric cam 4i rotates, the first support plate 4a is also moved to its lower position, which is off the undersurface of the micro-plate assembly 6. If the eccentric cam 4i further rotates to raise the second support plate 4e, on the other hand, the first support plate 4a is also raised by the spring 4c and situated close to the undersurface of the micro-plate assembly 6. In this state, the magnets 8 are situated individually in recesses 6d in the undersurface of the micro-plate assembly 6. Thereupon, the magnetic particles in the wells 6a are attracted to the magnets 8 and collected.

Figure 5A:
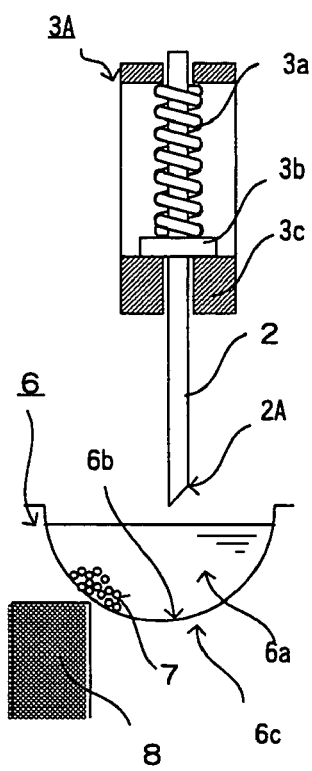
FIGS. 5A to 5C are views for illustrating the configuration and operation of an example of suction nozzle moving means of the drainage system of FIG. 1.
Figure 5B:
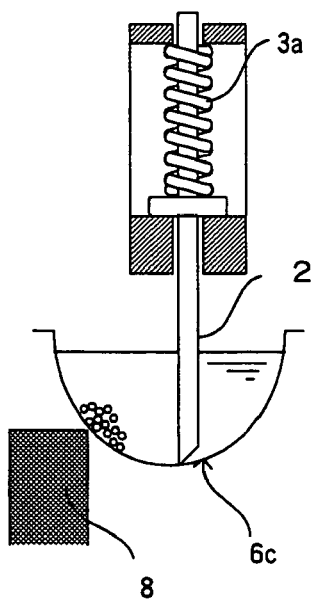
Figure 5C:
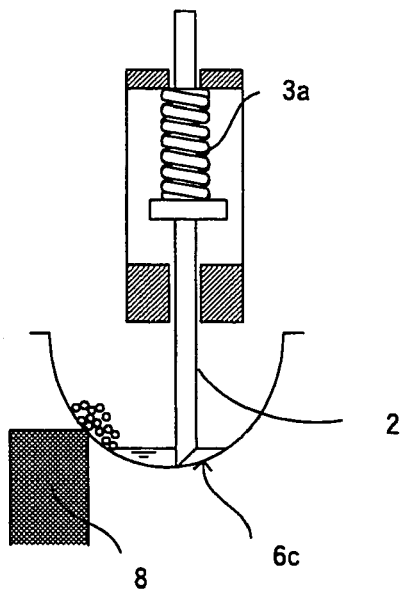

FIGS. 5A to 5C show a state in which magnetic particles are collected on the inner wall surface of a bottom portion 6b of one of the wells 6a.

If the second support plate 4e is further raised after the distance between the first and second support plates 4a and 4e is adjusted so that the plate 4a is brought into contact with bases 6c of the micro-plate assembly 6, the spring 4c contracts to absorb the ascent of the second support plate 4e (FIGS. 4C and 4D). Thus, each magnet 8 can be located on the base 6c in each corresponding recess 6d of the micro-plate assembly 6 as the spring 4c contracts without controlling the position of the second support plate 4e or the like.

Then, the suction nozzle moving means 3 causes the suction nozzles 2 to move to the wells 6a of the micro-plate assembly 6 (Step S6). FIGS. 5A to 5C and FIGS. 6A to 6C show two examples of the suction nozzle moving means 3.

In suction nozzle moving means 3A that is shown in FIGS. 5A to 5C, a suction nozzle 2 is slidably supported by a guide 3c, and is urged toward the micro-plate assembly 6 through a collar 3b by a spring 3a.

Figure 6A:
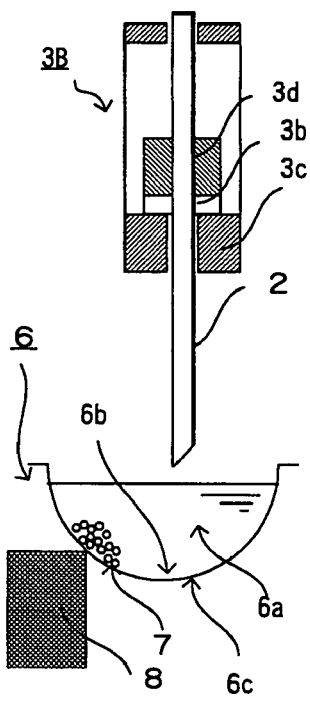
FIGS. 6A to 6C are views for illustrating the configuration and operation of another example of suction nozzle moving means of the drainage system of FIG. 1.
Figure 6B:
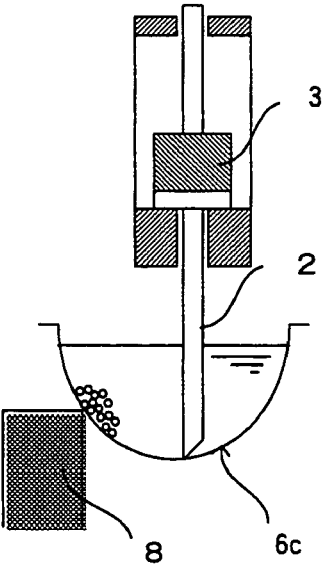
Figure 6C:
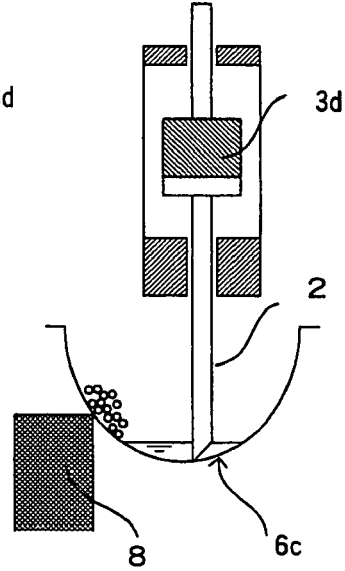

In suction nozzle moving means 3B that is shown in FIGS. 6A to 6C, a suction nozzle 2 is sidably supported by a guide 3c, and is urged toward the micro-plate assembly 6 through a collar 3b by a weight 3d.

In the description of the present embodiment to follow, the suction nozzle moving means 3 shown in FIGS. 5A to 5C are regarded as the suction nozzle moving means 3 of FIG. 1.

When the suction nozzle moving means 3 is moved toward the micro-plate assembly 6, a distal end 2A of the suction nozzle 2 approaches its corresponding well 6a of the micro-plate assembly 6 and abuts against the inner wall surface of the bottom portion 6b of the well 6a (Step S7).

If the suction nozzle moving means 3 is further moved toward the micro-plate assembly 6, the spring 3a absorbs this extra movement, so that the contact of the distal end 2A of the suction nozzle 2 with the bottom portion 6b can be maintained. Thus, the suction nozzle 2 can be easily positioned with respect to the micro-plate assembly 6 without subjecting the suction nozzle moving means 3 to any special position control.

Then, the switching valve 5*d* is shifted to connect the branch manifold 5*b* and the suction pump 5*c* or the buffer tank 5*h* (Step S8), and the suction pump 5*c* sucks the solution out of the wells 6*a* of the micro-plate assembly 6 (Step S9). During this suction, the cleaning fluid with which the pipes 5*a* are filled in advance are first sucked out, and at the same time, the solution in the wells 6*a* is sucked into the pipes 5*a*. During the suction, moreover, magnetic particles 7 in the wells 6*a* are collected and held by the magnets 8, and the solution can be sucked out at low suction speed as the pipes 5*a* are filled with the liquid. Thus, the magnetic particles 7 cannot be discharged by the suction by the suction nozzles 2.

If the capacity of the micro-plate assembly 6 is greater than that of the pipes 5*a* so that the pipes 5*a* are evacuated to cause the efficiency of suction through the other suction nozzles to lower during the suction, this suction efficiency can be increased by repeatedly filling the pipes 5*a* with the liquid in the aforesaid processes of Steps S1 to S3.

After the suction is finished, each suction nozzle 2 are separated from the micro-plate assembly 6 by the suction nozzle moving means 3 (Step S10). As this is done, the suction nozzle 2 is returned by the urging force of the spring 3*a* and located in its initial position by the collar 3*b*.

The switching valve 5*d* is shifted to connect the branch manifold 5*b* and the conveying pump 5*e* (Step S15), and the cleaning fluid 5*g* in the cleaning fluid vessel 5*f* is fed into the pipes 5*a* and the suction nozzles 2 by the pump 5*e*, whereby the pipes 5*a* and the nozzles 2 are cleaned (Step S12).

Figure 7:
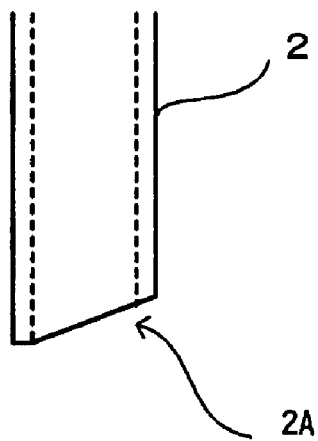
FIG. 7 is an enlarged partial view for illustrating the construction of the distal end portion of a suction nozzle of the drainage system of FIG. 1.

FIG. 7 shows an example of one suction nozzle 2 of FIG. 1 having a slanting distal end portion 2A. The slope of the distal end portion 2A of the nozzle 2 prevents the opening of the end portion 2A from being closed even if the end portion 2A touches the bottom portion of its corresponding well 6*a*.

Figure 8A:
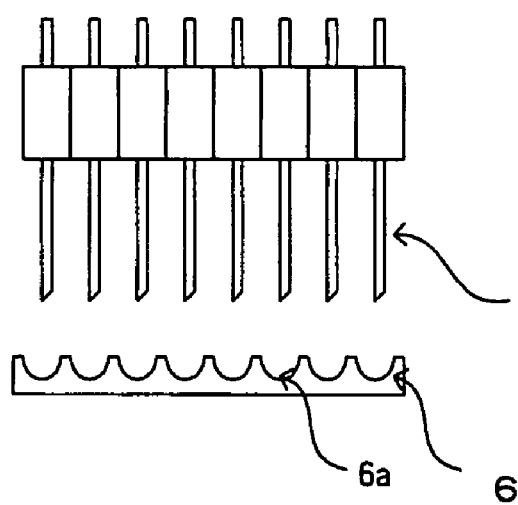
FIGS. 8A and 8B are views for illustrating a modification of suction nozzles of the drainage system of FIG. 1.
Figure 8B:
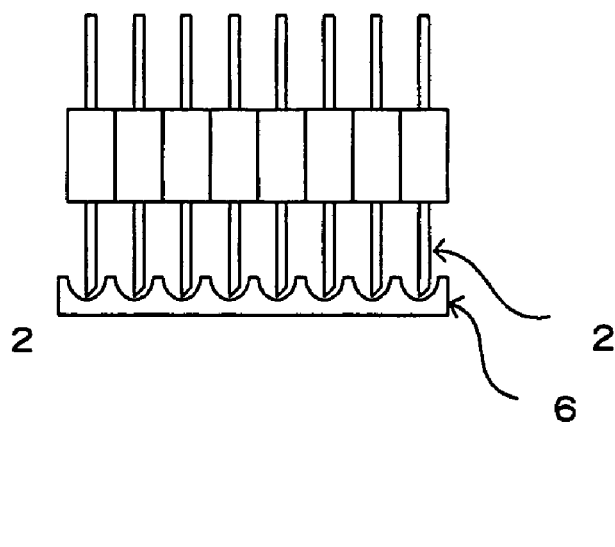

FIGS. 8A and 8B show a plurality of suction nozzles 2 that are arranged with suction nozzle moving means 3 connected to one another. If the positions (heights) of the respective distal end portions of the nozzles 2 with respect to the micro-plate assembly 6 are not equal, according to this arrangement, the support means and the urging means of the suction nozzle moving means 3 can satisfactorily bring the nozzle end portions into contact with the wells 6*a* without requiring any special position control.

If the conveying pump 5*e* of FIG. 1 is a constant delivery pump, a reagent can be injected through each suction nozzle 2 at a fixed rate. Even in the case where a plurality of suction nozzles 2 are arranged in the manner as shown in FIG. 8A, the reagent can be distributed in desired ratios to a plurality of micro-plates 6 by adjusting the respective resistances of the branch manifold 5*b* and the pipes 5*a*.

According to the embodiment of the present invention, the suction nozzle moving means, magnetic particle holding means, solution discharge means, or combinations of these means can be used easily to carry out suction and discharge without requiring any special control for positioning.

Further, the solution can be sucked and discharged simultaneously through a plurality of suction nozzles, and these nozzles can be cleaned simultaneously.

According to the drainage system of the present invention, as described herein, processes for suction, discharge, separation, etc. can be carried out with use of a simple mechanism.

What is claimed is:

1. A drainage system comprising:

a suction nozzle for sucking and discharging a solution from a vessel;

a magnet; and magnet moving means for supporting the magnet so as to be movable toward and away from the vessel, said magnet moving means including two support plates with a spring interposed there between, the magnet being capable of holding magnetic particles in a given position in the vessel by being moved toward the vessel by the magnet moving means.

2. A drainage system comprising:

a buffer tank;

a plurality of suction nozzles for sucking and discharging a solution from a vessel;

a branch manifold connected to the suction nozzles through pipes;

a suction pump connected to the buffer tank for suction of the solution from the suction nozzles through the branch manifold;

liquid conveying means for feeding a liquid through said branch manifold and into the pipes located between the branch manifold and each of the suction nozzles, thereby filling the pipes with the liquid; and a switching valve connected to the buffer tank, the liquid conveying means and the branch manifold, the suction pump being capable of operating so that the solution in the vessel can be sucked out simultaneously from each of the suction nozzles then through the branch manifold;

wherein the buffer tank has two ports, a first port is connected to the suction pump and a second port is connected to the switching valve, wherein said switching valve allows for said liquid filling of said pipes via said liquid conveying means when in a first position and suction from said vessel when in a second position, and wherein said buffer tank is disposed between said branch manifold and said suction pump.

3. A drainage system comprising:

a plurality of suction nozzles for sucking and discharging a solution from a vessel;

support means for supporting the suction nozzles, for movement toward the vessel;

suction nozzle moving means including urging means for urging the suction nozzles toward the vessel and a guide, located beneath the urging means, for slidably supporting the plurality of suction nozzles;

a magnet;

magnet moving means for supporting the magnet so as to be movable toward and away from the vessel, said magnet moving means including two support plates with a spring interposed there between;

a branch manifold connected to the suction nozzles through pipes;

a suction pump for suction from the suction nozzles through the branch manifold; and liquid conveying means for feeding a liquid through said branch manifold and into the pipes located between the branch manifold and each of the suction nozzles, thereby filling the pipes with the liquid; and a switching valve connected to each of said manifold, liquid conveying means and suction pump, the suction nozzle moving means being capable of positioning the suction nozzle with the distal end thereof in contact with the inner wall surface of the vessel, the magnet being capable of holding magnetic particles in a given position in the vessel by being moved toward the vessel by the magnet moving means, and the suction pump being capable of operating so that the solution in the vessel can be sucked out simultaneously from each of the suction nozzles then through the branch manifold, and wherein said switching means allows said liquid filling of said pipes via said liquid conveying means when in a first position and suction from said vessel when in a second position, and wherein said suction nozzle moving means also includes a collar located beneath the urging means.

* * * * *